(12) United States Patent
Haras et al.

(10) Patent No.: US 7,453,975 B2
(45) Date of Patent: Nov. 18, 2008

(54) OPERATING METHOD FOR AN X-RAY MACHINE

(75) Inventors: Gabriel Haras, Mücke (DE); Matthias Niethammer, Möhrendorf (DE)

(73) Assignee: Siemens Aktiengesellschaft, Munich (DE)

( * ) Notice: Subject to any disclaimer, the term of this patent is extended or adjusted under 35 U.S.C. 154(b) by 144 days.

(21) Appl. No.: 11/643,707

(22) Filed: Dec. 22, 2006

(65) Prior Publication Data

US 2007/0147578 A1 Jun. 28, 2007

(30) Foreign Application Priority Data

Dec. 23, 2005 (DE) .................. 10 2005 061 847

(51) Int. Cl.
*G01N 23/00* (2006.01)
*G01N 23/06* (2006.01)

(52) U.S. Cl. ............................. 378/8; 378/51
(58) Field of Classification Search ..................... 378/4, 378/8, 19, 15, 51, 162, 165
See application file for complete search history.

(56) References Cited

U.S. PATENT DOCUMENTS 4,943,987 A 7/1990 Asahina et al.
7,020,511 B2* 3/2006 Boyd et al. .................. 600/428
7,154,987 B2* 12/2006 Rubin et al. .................... 378/8

FOREIGN PATENT DOCUMENTS

DE 38 26 550 C2 1/1994

OTHER PUBLICATIONS

German Office Action.

\* cited by examiner

*Primary Examiner*—Irakli Kiknadze
(74) *Attorney, Agent, or Firm*—Harness, Dickey & Pierce, P.L.C.

(57) ABSTRACT

An operating method for an X-ray machine is disclosed for carrying out a preliminary examination by using a contrast agent, in the case of which a number of heartbeats are determined within a time interval between a first instant of a contrast agent administration and a second instant of a maximum in a concentration of the contrast agent. An operating method for the X-ray machine is also disclosed for carrying out a main examination by using a contrast agent, in the case of which the scanning of the examination region is not started until the number of heartbeats coincides with a preset value such that the scanning is performed at a high concentration of the contrast agent inside the examination region, without the need to adapt the value to the heart rate currently present.

16 Claims, 3 Drawing Sheets

OPERATING METHOD FOR AN X-RAY MACHINE

PRIORITY STATEMENT

The present application hereby claims priority under 35 U.S.C. §119 on German patent application number DE 10 2005 061 847.2 filed Dec. 23, 2005, the entire contents of which is hereby incorporated herein by reference.

FIELD

Embodiments of the invention generally relate to an operating method for an X-ray machine for carrying out a preliminary examination. For example, it may relate to an X-ray machine for carrying out a preliminary examination in which, at consecutive instants, attenuation values are acquired at a scanning position as a measure of the concentration of a contrast agent propagating in the body of a patient. Embodiments of the invention further generally relate to an operating method for an X-ray machine. For example, it may relate to an operating method for an X-ray machine for carrying out a main examination in which an examination region of a patient is scanned by way of a recording system of the X-ray machine by using a contrast agent.

BACKGROUND

The contrast in an X-ray image is usually caused by different attenuation properties of the substances relative to the X-radiation produced by an X-ray machine. When examining a patient it is possible on the basis of the different attenuation properties of bone tissue and soft part tissue to analyze the structure of the bone in the body interior of a patient on the basis of the contrast. Organs or vessels having an attenuation property similar to the surroundings cannot be examined in a conventional way because of too low a contrast.

For this reason, a contrast agent is used when examining an organ supplied with blood, for example, a heart or a liver. The contrast agent exhibits a different attenuation property by comparison with the surrounding tissue and so a visible contrast is produced between the organ and the surroundings in the image.

The propagation of the contrast agent in the patient's body is a highly dynamic process. After a certain time, the concentration of the contrast agent in an examination region being viewed rises steeply at first, reaches a maximum and subsequently falls back again. During a main examination the scanning of the examination region is not started immediately, but only after a delay time after the instant of contrast agent administration, such that the examination region has a high concentration of the contrast agent during scanning. The delay time is determined at the beginning of each examination by means of a preliminary examination in which a slight quantity of the contrast agent is fed to the patient, and in which attenuation values at consecutive instants are acquired as a measure of the concentration of the contrast agent at the scanning position. The delay time results in this case from the time interval between the contrast agent administration and the observed maximum in the attenuation values.

SUMMARY

In at least one embodiment of the present invention, a method for an X-ray machine is specified with the aid of which the preconditions are created for being able, with simple devices/methods, to improve a temporal coordination between scanning an examination region and administering contrast agent.

As a physiological parameter of the patient, during an examination and between different examinations the heart rate can fluctuate very strongly owing to stress or as occasioned by an administered drug. Changes in heart rate lead to changes in the rate of propagation of the contrast agent. For this reason, the instant of maximum concentration of the contrast agent inside the examination region can shift from examination to examination. In this situation, it is necessary before beginning a main examination to undertake an adaptation when coordinating between contrast agent administration and scan on the basis of a delay time determined in advance. However, this can be carried out only with a very high outlay.

The inventors have recognized, in at least one embodiment, that the temporal coordination between the contrast agent administration and the scan can be substantially simplified by using a number of heartbeats of the patient instead of a delay time as the measurement variable for determining the starting instant of the scan. Specifically, with each heartbeat a comparable quantity of blood is transported such that the instant of maximum contrast in the examination region is reached independently of the absolute value of the heart rate essentially after a specific number of heartbeats.

Consequently, according to at least one embodiment of the invention, an operating method for an X-ray machine for carrying out a preliminary examination is proposed in the case of which at consecutive instants attenuation values are acquired at a scanning position as a measure of the concentration of a contrast agent propagating in the body of a patient, there being determined, for a main examination that is to be to be carried out, a number of heartbeats of the patient within a time interval that is defined by a first instant of a contrast agent administration and a second instant of a local maximum in the attenuation values.

The number of heartbeats determined inside the time interval provides the preconditions for being able to carry out the temporal coordination between the contrast agent administration and start of the scan with the aid of simple means during a main examination without the need to adapt the measurement variable used for the coordination with regard to the heart rate. After the contrast agent administration, the only requirement is also to count the heartbeats and compare them, as threshold value, with the number of heartbeats determined in the preliminary examination.

The situation is different when the position of the examination region in the main examination deviates substantially from the position of the scanning position in the preliminary examination. In this case, scanning is started when the number of heartbeats also counted in the main examination coincides with a value dependent on the position of the examination region and on the number of heartbeats determined in the preliminary examination. If, for example, the examination region is arranged near to the heart in relation to the scanning position in the preliminary examination, the number determined must be corrected toward smaller values by a value dependent on the distance between the examination region and heart.

The instant of scanning is adapted automatically to the heart rates occurring during the examination. Even in the case of arrhythmic beating of the heart, it is ensured that scanning is started after the contrast agent administration precisely when the concentration is at a maximum in the examination region. Thus, the beginning of the scan does not, as in the case of a determined delay time, take place after a preset fixed time interval. The instant occurs for each examination entirely individually as a function of the physiological situation of the patient that is present.

In order to reduce the applied X-radiation, the preliminary examination is carried out with an intensity of x-radiation that is lower by comparison with the main examination.

The local maximum in the attenuation values can be determined with particular ease whenever the instants for acquiring the attenuation values are arranged equidistantly on a time axis. In this case, the curve profile of the attenuation values can be approximated by a higher order polynomial. The local maximum in the attenuation values can subsequently be determined advantageously on the basis of the approximated curve profile, for example by evaluating the first and second derivatives of the polynomial.

In an advantageous refinement of at least one embodiment the invention, the number of heartbeats for the main examination to be carried out is stored for the purpose of quick availability. The storage is advantageously performed in an electronic patient file such that the number of heartbeats can easily be evaluated in conjunction with other physiological parameters such as for example, weight and age, thus enabling the patient's state of health to be deduced.

The number of heartbeats is preferably multiplied by an acquired ejection fraction of the heart as a measure of a reference volume. The reference volume represents the total volume of blood that is pumped through the heart between the contrast agent administration and maximum in the contrast at the scanning position. The reference volume as measured variable that is used to start scanning in a main examination therefore takes account of the currently present physiological state of the heart and facilitates a further improvement in the coordination between the contrast agent administration and scanning.

The reference volume is preferably stored for a quick availability for the main examination to be carried out. The storage can likewise advantageously be performed in an electronic patient file such that it is possible to evaluate the reference volume in conjunction with other physiological parameters in order to determine the patient's state of health in a simple way.

In at least one embodiment, an operating method is disclosed for an X-ray machine for carrying out a main examination in which an examination region of a patient is scanned via a recording system of the X-ray machine by using a contrast agent, a number of heartbeats of the patient being determined from a first instant of a contrast agent administration, and a continuous comparison being undertaken between the number and a preset value, the scanning of the examination region not being started until the number of heartbeats coincides with the preset value such that the scanning is performed at a high concentration of the contrast agent inside the examination region. There is thus no need to adapt the preset value from examination to examination for the purpose of temporal coordination between the contrast agent administration and scanning.

The preset value preferably corresponds to a number of heartbeats that is determined using an operating method for an X-ray machine for carrying out a previously described preliminary examination.

In an advantageous refinement of at least one embodiment of the invention, the determined number of heartbeats is multiplied by an acquired ejection fraction of the heart during the main examination. The preset value corresponds in this case to a reference volume that is determined in the course of a preliminary examination, that corresponds to the quantity of blood that is pumped through the heart between contrast agent administration and start of scanning.

BRIEF DESCRIPTION OF THE DRAWINGS

Example embodiments of the invention and a further refinement of the invention are discussed below and are illustrated in the following schematics, in which.

DETAILED DESCRIPTION OF THE EXAMPLE EMBODIMENTS

Figure 1:
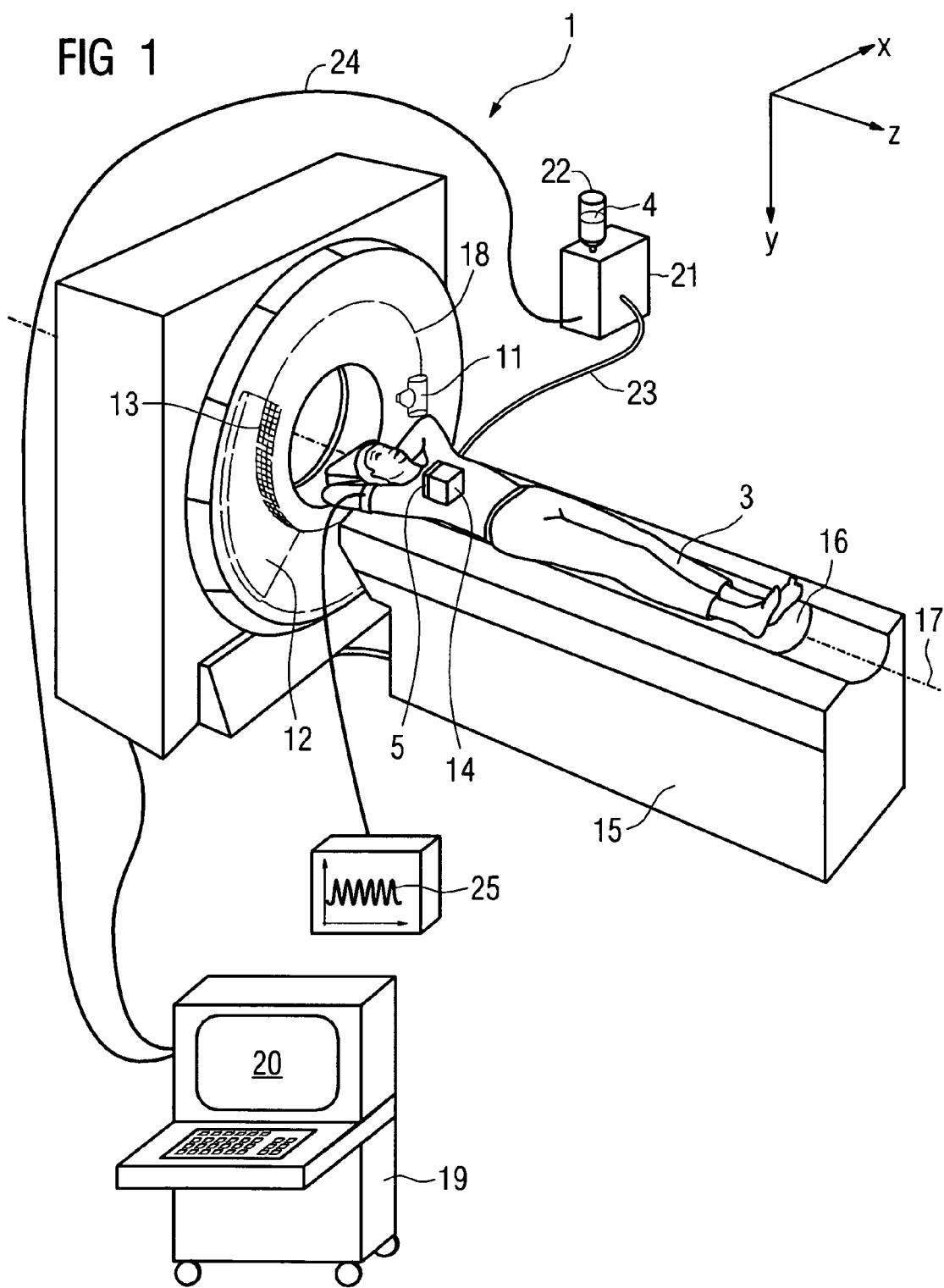
FIG. 1 shows a perspective illustration of an X-ray machine that is suitable for executing an embodiment of the inventive operating method for a preliminary and a main examination by using a contrast agent.

The terminology used herein is for the purpose of describing particular embodiments only and is not intended to be limiting of the present invention. As used herein, the singular forms "a", "an" and "the" are intended to include the plural forms as well, unless the context clearly indicates otherwise. It will be further understood that the terms "includes" and/or "including", when used in this specification, specify the presence of stated features, integers, steps, operations, elements, and/or components, but do not preclude the presence or addition of one or more other features, integers, steps, operations, elements, components, and/or groups thereof.

In describing example embodiments illustrated in the drawings, specific terminology is employed for the sake of clarity. However, the disclosure of this patent specification is not intended to be limited to the specific terminology so selected and it is to be understood that each specific element includes all technical equivalents that operate in a similar manner.

Referencing the drawings, wherein like reference numerals designate identical or corresponding parts throughout the several views, example embodiments of the present patent application are hereafter described.

Shown in a perspective view in FIG. 1 is an X-ray machine, here a computed tomography unit provided with the reference numeral 1, that is suitable for carrying out an embodiment of the inventive operating method for a preliminary and a main examination for examining a patient 3 while using a contrast agent 4.

The computed tomography unit 1 is assigned a bearing apparatus 15 with a movable table plate 16 on which the patient 3 can be borne. The table plate 16 can be adjusted in the direction of the axis of rotation 17 such that an examination region 14 associated with the patient 3 can be moved into the measuring range of a recording system 11, 12 through an opening in the housing of the computed tomography unit 1. The patient 3 and the recording system 11, 12 can in this way be adjusted relative to one another in the direction of the axis of rotation such that different scanning positions can be adopted.

In order to acquire projections, the recording system 11, 12 has an emitter 11 in the form of an X-ray tube, and a detector 12 arranged opposite the latter, the detector 12 being of arcuate design and including a number of detector elements 13 lined up to form detector rows. The emitter 11 generates radiation in the form of a fan-shaped X-ray beam that penetrates the measuring region and subsequently strikes the detector elements 13 of the detector 12. The detector elements 13 produce an attenuation value 6 depending on the attenuation of the X-radiation passing through the measuring region. The conversion of the X-radiation into attenuation values 6 is performed in each case, for example, by way of a photodiode optically coupled to a scintillator, or by means of a directly converting semiconductor. The detector 12 in this way produces a set of attenuation values that is also denoted as a projection.

The recording system is arranged rotatably on a gantry 18 such that projections can be acquired from different projection directions. Depending on the operating mode set for the computed tomography unit 1, the scanning is performed with a permanently set or variable projection direction in conjunction with a permanently set or variable scanning position. By way of example, projections from a multiplicity of different projection directions at various positions along the axis of rotation 17 or along the patient 3 are acquired by rotating the gantry 18 while simultaneously continuously advancing the patient 3 in the direction of the axis of rotation 17. The projections of the recording system 11, 12 that are obtained in this way by spiral scanning are transmitted to an arithmetic logic unit 19 and converted to an image that can be displayed on a display unit 20. The image can be, for example, a slice image or volume image of an examination region 14.

In order to examine organs supplied with blood, for example a heart or a liver or a vessel, the patient 3 can be injected if required with a contrast agent 4 by way of a contrast agent device 21 in order to increase the visible contrast against the surrounding soft part tissue. The contrast agent 4 is pumped in an automated and time-controlled fashion from a supply container 22 via a contrast agent tube 23 in an adjustable quantity and at an adjustable flow rate into a vein of the patient 3. The parameters for the administration of contrast agent can be prescribed by the arithmetic unit 19 by way of an electrical connection 24 between the arithmetic unit 19 and the contrast agent device 21.

A pulse meter 25 enables heartbeats 6 of the patient 3 to be acquired in parallel with scanning. The arithmetic unit 19 is connected electrically to the pulse meter 25 such that after the instant of contrast agent administration the number of heartbeats 6 can also be counted continuously in a computer-aided fashion.

Figure 2:
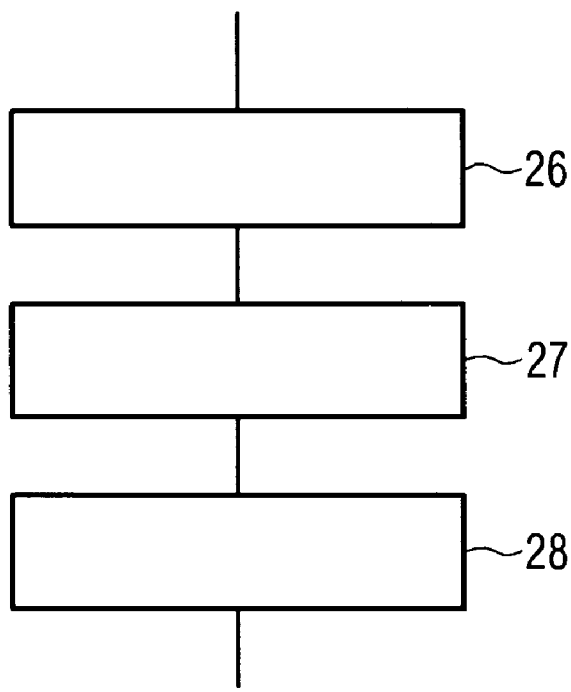
FIG. 2 shows a block diagram of a first operating method for carrying out a preliminary examination for determining the number of heartbeats for the purpose of temporal coordination of a contrast agent administration and a scan.

FIG. 2 shows a block diagram of a first operating method for carrying out a preliminary examination for determining the number of heartbeats 6 for the purpose of temporal coordination between the contrast agent administration and scanning. The individual method steps of the preliminary examination, and also of the main examination to be carried out later, can be executed by means of a program stored on the arithmetic unit 19 and which can be activated by a user.

In a first method step 26, a scanning position 5 is assumed for acquiring the attenuation values. The selection of the scanning position 5 is, for example, performed in this case by marking a position in an overview image displayed on the display unit 19, the adjusting parameters for the table plate 16 and the recording system 11 or 12 subsequently being determined as a function of the marking.

As a rule, the scanning position 5 is arranged inside or directly upstream of the examination region 14 to be scanned during a main examination, and so the temporal changes in concentration of the contrast agent 4 at the scanning position 5 correspond substantially to those in the examination region 14. It is also self-evidently possible to assume a scanning position 5 that differs from the position of the examination region 14. In this case, it is necessary to correct the number of heartbeats to be determined at the start of scanning when carrying out the main examination. The number can be corrected, for example, by weighting the number of heartbeats as a function of the distance between the scanning position 5 of the preliminary examination and the position of the examination region 14.

In a second method step 27, a slight quantity of the contrast agent 4 is injected with the aid of the contrast agent device 21. At the same time as the contrast agent administration, the attenuation values at the scanning position 5 are acquired, and the heartbeats of the patient are acquired, each attenuation value and each heartbeat being assigned a timestamp. The attenuation values are acquired for the purpose of reducing an applied X-ray dose during an intensity of the X-radiation that is lower by comparison with the main examination. The scanning is performed in this example in the one-second cycle at equidistant instants until the maximum in the attenuation values has been traversed.

Figure 3:
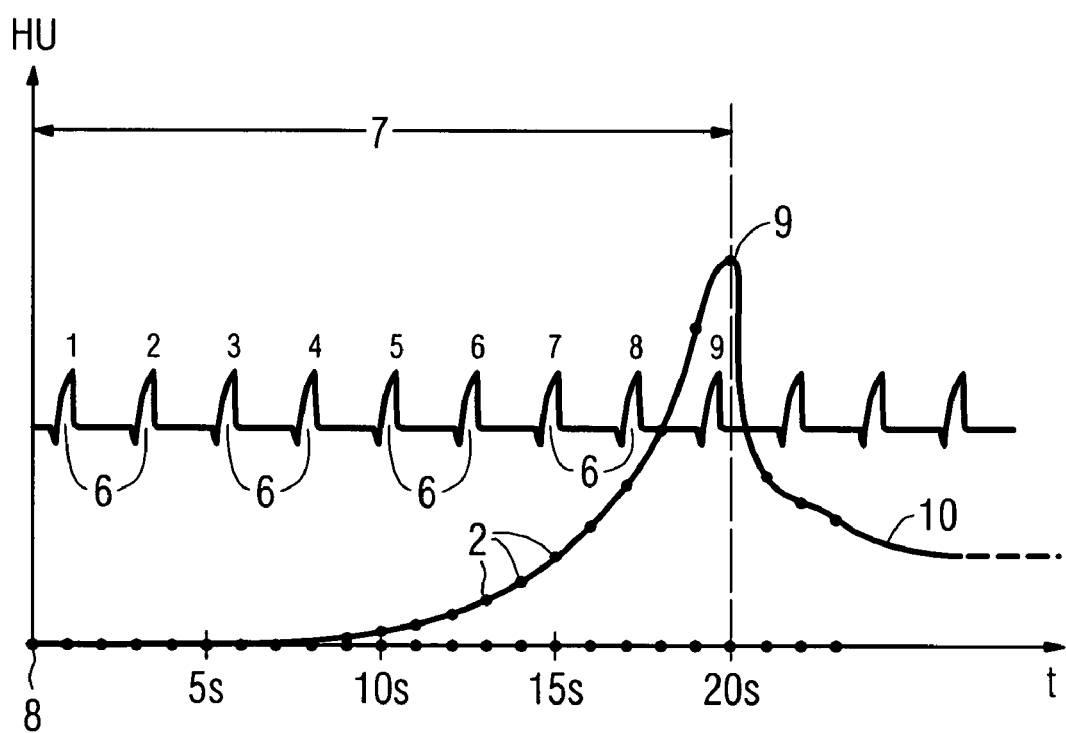
FIG. 3 shows a diagram in which the relationship between acquired attenuation values and heartbeats of a patient is illustrated.

In a third method step, an approximation method known per se is used to approximate the acquired attenuation values 2 to a curve profile 10 illustrated in FIG. 3, for example to a curve profile of a higher-order polynomial. The attenuation values are plotted along the y-axis in Hounsfield units (HU). The x-axis corresponds to the elapse of time in seconds. Likewise depicted in FIG. 3 is the time profile of a signal of an ECG 29 that serves for acquiring the heartbeats 6. No unit is specified in the direction of the y-axis for the signal of the ECG 29. Only the characteristic curve profile of the signal is reproduced.

The local maximum 9 can be determined from the determined curve profile 10 of the attenuation values 2, for example by evaluating the first and second derivative of the curve profile of the attenuation values. The instant of the local maximum 9 corresponds to the instant of the highest concentration of the contrast agent 4 at the scanning position 5. The number of heartbeats 6 is subsequently determined within the time interval 7 between the instant of the contrast agent administration 8 and the instant of the local maximum 9 of the attenuation values 2.

In the example shown, the time interval 7 between the contrast agent administration 8 and the maximum 9 in the attenuation values 2 is 20 seconds. A total of nine heartbeats are completed within this time interval 7.

In pictorial terms, each heartbeat 6 can be assigned a specific concentration of the contrast agent 4 at the scanning position 5, since an essentially permanently defined quantity of blood is transported through the blood circulation with each beat of the heart. An arrhythmic beating of the heart has the effect that the curve profile 10 is either compressed or stretched in parts such that the instant of the local maximum 9 can be displaced along the time axis from examination to examination. However, irrespective of the fluctuations in the heart rate during an examination, the maximum 9 is reached essentially always after the number of heartbeats 6 determined during the preliminary examination. The result of this is to dispense with an operating parameter, for example a determined delay time between the contrast agent administration 8 and maximum 9 in the observed attenuation values 2 being adapted, in a way that is complicated to carry out, to the currently present heart rate at the start of scanning for a main examination.

As an option, an ejection fraction of the heart that serves for calculating a reference volume can be determined in addition before beginning an examination or in relation to each individual heartbeat. The ejection fraction corresponds to the quantity of blood that is ejected from the left-hand ventricle of the heart with each heartbeat. It is calculated from the diastolic and systolic volumes in accordance with the following equation:

$$EF=(EDV-ESV)/EDV, \text{ where}$$

EF represents the ejection fraction,
EDV represents the diastolic volume, and
ESV represents the systolic volume.

The diastolic and systolic volumes can be determined with the aid of echocardiography. Multiplying the ejection fraction by the number of heartbeats or by the respectively corresponding heartbeat within the previously determined time interval results in a reference volume that corresponds to a quantity of blood that is pumped through the heart within the time interval from the beginning of the contrast agent administration and up to the maximum in the concentration. The reference volume takes account of the currently present physiological state of the heart. Both the number of heartbeats and the reference volume are suitable for controlling the starting instant of scanning during a main examination.

The determined number of heartbeats 6 and/or the determined reference volume can be stored on the arithmetic unit 19, for example in an electronic patient file, and can be processed with other physiological data stored therein in order to determine a state of health.

Figure 4:
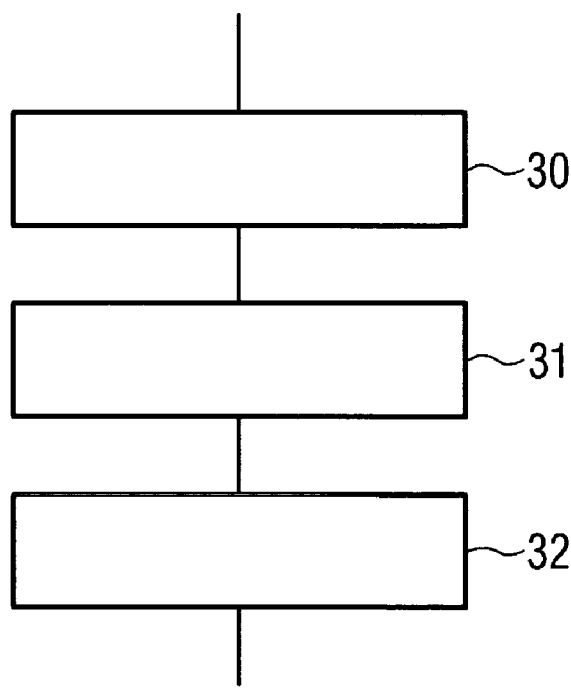
FIG. 4 shows a block diagram of a second operating method for carrying out a main examination, in which the contrast agent administration and scanning are coordinated on the basis of acquired heartbeats.

FIG. 4 illustrates in a block diagram an embodiment of a second operating method for carrying out a main examination. In a first method step 30, the initial position of the scan of the examination region 14 is adopted by adjusting the table plate 16 and the recording system 11, 12. Subsequently, the operating parameter required to start the scan is loaded as a preset value in the form of the number of heartbeats 6 determined in the preliminary examination. In a second method step 31, the contrast agent 4 is injected by way of the contrast agent device 21. At the same time, the acquisition of the heartbeats and the continuous comparison of the determined heartbeats with the preset value begin.

When there is equality, the scanning of the examination region 14 is started in a third method step 32, and so the scanning is performed to a maximum concentration in the contrast agent 4 in the examination region 14. The starting instant of the scan can also optionally be controlled on the basis of the previously determined reference volume, that is to say the quantity of blood pumped through the blood circulation up to when the maximum in the concentration in the contrast agent 4 is reached, and on the basis of the heartbeats, acquired during the main examination, multiplied by the ejection fraction.

At least one embodiment of the invention can be summarized as follows:

At least one embodiment of the invention relates to an operating method for an X-ray machine 1 for carrying out a preliminary examination by using a contrast agent 4, in the case of which a number of heartbeats 6 are determined within a time interval 7 between a first instant of a contrast agent administration 8 and a second instant of a maximum 9 in a concentration of the contrast agent 4.

At least one embodiment of the invention also relates to an operating method for the X-ray machine 1 for carrying out a main examination by using a contrast agent 4, in the case of which the scanning of the examination region 14 is not started until the number of heartbeats 6 coincides with a preset value such that the scanning is performed at a high concentration of the contrast agent 4 inside the examination region 14, without the need to adapt the value to the heart rate currently present.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. An operating method for an X-ray machine for carrying out a preliminary examination, the method comprising:
   acquiring, at consecutive instants, attenuation values at a scanning position as a measure of concentration of a contrast agent propagating in the body of a patient; and
   determining, for a main examination that is to be carried out, a number of heartbeats of the patient as measured variable for determining a starting instant of a scan, this being done within a time interval defined by a first instant of a contrast agent administration and a second instant of a local maximum in the acquired attenuation values.

2. The method as claimed in claim 1, wherein the preliminary examination is carried out with an intensity of x-radiation that is lower by comparison with the main examination.

3. The method as claimed in claim 1, wherein the instants for acquiring the attenuation values are arranged equidistantly on a time axis.

4. The method as claimed in claim 1, wherein the local maximum in the attenuation values is determined by virtue of the fact that a curve profile of the contrast agent concentration is calculated from the acquired attenuation values, and a local maximum in the curve profile is subsequently determined.

5. The method as claimed in claim 4, wherein the curve profile constitutes a higher order polynomial.

6. The method as claimed in claim 1, wherein the number of heartbeats for the main examination to be carried out is stored.

7. The method as claimed in claim 6, wherein the storage is performed in an electronic patient file.

8. The method as claimed in claim 1, wherein the number of heartbeats is multiplied by an acquired ejection fraction of the heart as a measure of a reference volume.

9. The method as claimed in claim 8, wherein the reference volume for the main examination to be carried out is stored.

10. The method as claimed in claim 9, wherein the storage is performed in an electronic patient file.

11. The method as claimed in claim 8, wherein the storage is performed in an electronic patient file.

12. The method as claimed in claim 2, wherein the instants for acquiring the attenuation values are arranged equidistantly on a time axis.

13. The method as claimed in claim 2, wherein the local maximum in the attenuation values is determined by virtue of the fact that a curve profile of the contrast agent concentration is calculated from the acquired attenuation values, and a local maximum in the curve profile is subsequently determined.

14. An operating method for an X-ray machine for carrying out a main examination, comprising:
   scanning an examination region of a patient is scanned by way a recording system of the X-ray machine, by using a contrast agent;
   determining a number of heartbeats of the patient from a first instant of a contrast agent administration; and
   undertaking a continuous comparison between the determined number and a preset value, the scanning of the examination region not being started until the number of heartbeats coincides with the preset value such that the scanning is performed at a high concentration of the contrast agent inside the examination region.

15. The method as claimed in claim 14, wherein the preset value corresponds to a measured variable that is determined using an operating method for the X-ray machine for carrying out a preliminary examination by:
   acquiring, at consecutive instants, attenuation values at a scanning position as a measure of concentration of a contrast agent propagating in the body of a patient; and
   determining, for a main examination that is to be carried out, a number of heartbeats of the patient as measured variable for determining a starting instant of a scan, this being done within a time interval defined by a first instant of a contrast agent administration and a second instant of a local maximum in the acquired attenuation values.

16. The method as claimed in claim 14, wherein, before the comparison the number of heartbeats is multiplied by an acquired ejection fraction of the heart, and the preset value corresponds to a reference volume that is determined in the course of a preliminary examination by:
   acquiring, at consecutive instants, attenuation values at a scanning position as a measure of concentration of a contrast agent propagating in the body of a patient; and
   determining, for a main examination that is to be carried out, a number of heartbeats of the patient as measured variable for determining a starting instant of a scan, this being done within a time interval defined by a first instant of a contrast agent administration and a second instant of a local maximum in the acquired attenuation values, wherein the number of heartbeats is multiplied by an acquired ejection fraction of the heart as a measure of a reference volume.

* * * * *